United States Patent [19]

Ruwart

[11] 4,374,856
[45] Feb. 22, 1983

[54] LIVER CYTOPROTECTION USING PGE'S

[75] Inventor: Mary J. Ruwart, Kalamazoo, Mich.

[73] Assignee: The Upjohn Company, Kalamazoo, Mich.

[21] Appl. No.: 185,837

[22] Filed: Sep. 10, 1980

[51] Int. Cl.$^3$ .................. A61K 31/19; A61K 31/215
[52] U.S. Cl. ........................................ 424/317; 424/305
[58] Field of Search .......................... 424/305, 37, 285

[56] References Cited

U.S. PATENT DOCUMENTS 4,073,938 2/1978 Valcavi .

FOREIGN PATENT DOCUMENTS 832229 12/1975 Belgium .

OTHER PUBLICATIONS

A. Araki, et al., Am. J. Physiol. Soc., 7:H176–H181 (1980).
T. Mach, et al., J. for Clin. Res. and Practices Abst. of Xi Int. Cong. of Gastroenterol. 8–13 Jun. 1980 (Hamburg), F 5.14.
Derwent Farmdoc Abstract 00122X/01.
Tomasi et al.–Lipoprotein Metabolism and Endocrine Regulation (1979), pp. 279–287.
Tomasi et al.–Chem. Abst., vol. 91, (1979), p. 49704a.
Zipser et al.–Clin. Res., vol. 25, (1977), p. 151A.
Arieff et al.–Am. J. of Med., vol. 56, May 1974, pp. 695–703.
Flamenbaum et al.–Int'nat. Conf., Kidney in Liver Disease, Miami 1976, (pub. 1978), pp. 285–298.

Primary Examiner—Sam Rosen
Attorney, Agent, or Firm—Lawrence T. Welch

[57] ABSTRACT

The present invention provides a method for treatment of hepatic diseases which comprises administering a hepatocytoprotective prostaglandin to a mammal who suffers from or is particularly succeptible to said hepatic diseases.

7 Claims, No Drawings

LIVER CYTOPROTECTION USING PGE'S

DESCRIPTION

BACKGROUND OF THE INVENTION

The present invention relates to a novel method of treatment. More particularly, the present invention relates to a novel method for preventing or treating hepatic diseases.

Most particularly, the present invention relates to the surprising and unexpected effect of certain prostaglandins and prostaglandin analogs in treating liver diseases.

Liver diseases take a number of forms including jaundice, hepititis, cirrhosis, circulatory disorders, fatty liver, amyloid disease, neoplasms, and biliary disorders. See, The Merck Manual, 12th Edition, 762–788 (1972).

Among the most frequently occurring liver diseases are cirrhosis of the liver and fatty liver disease. Cirrhosis of the liver is caused from a variety of sources including alcoholism, prolonged biliary tract obstruction, submassive hepatic necrosis of viral hepititis, malnutrition, hemochromatosis, hepatolenticular degeneration (Wilsons Disease), congestive heart failure, and syphilis.

Two types of cirrhosis are known. Portal cirrhosis (also known as Laennec's, fatty, nutritional, or alcoholic cirrhosis) is characterized by uniform diffused small modules, fine fibrosis, and pseudolobule formation, accompanied by extensive fatty vacuolization. This is a more common form of cirrhosis. Postnecrotic cirrhosis (also known as post-hepatic, toxic, healed yellow atrophy, or macronodular cirrhosis) is characterized by irregular large nodules, broad bands of scar tissue, and preservation of some normal liver architecture. These two forms of cirrhosis may be variations of a single disease process or different entities. See The Merck Manual, supra.

Fatty liver disease is caused by excessive fat intake, ingestion of intoxicants, (e.g., alcohol, carbon tetrachloride, and chloroform), chronic infections, metabolic disorders, and anemias. The symptoms are not specific and cannot be distinguished from those of other chronic diseases such as cirrhosis, chronic passive congestion, amyloidosis, and leukemia.

The treatment for fatty liver disease and cirrhosis generally consists of a protein rich diet supplemented by vitamins and the like. Strict abstinence from alcohol is essential.

Pharmacological agents which prevent necrotic changes in cells are known as cytoprotective agents. Numerous gastrointestinal cytoprotective effects of the prostaglandins are known. See for example U.S. Pat. No. 4,083,998 (Robert, "Treatment of Inflammatory Disease of the Mammalian Large Intestine with Cytoprotective Prostaglandins"), issued April 11, 1978, U.S. Pat. No. 4,081,553 (Robert, "Cytoprotective Prostaglandins for Use in Intestinal Diseases"), issued March 28, 1978, and U.S. Pat. No. 4,097,603 (Robert, "Gastric Cytoprotection with Non-Antisecretory Doses of Prostaglandins"), issued June 27, 1978. Agents which are specific for the reduction of liver damage are referred to herein as hepatocytoprotective agents.

The prostaglandins are derivatives of prostanoic acid. A trivial system of nomenclature has been devised, which classifies the prostaglandins according to the substituents on the cyclopentane ring. See, N. A. Nelson, Journal of Medicinal Chemistry, 17:911 (1974). For a further discussion of the prostaglandins, see Bergstrom, et al., Pharmacol. Rev. 20:1 (1968).

PRIOR ART

H. Araki, et al., Am. J. Physiol. Soc. 7:H176–H181 (1980), in a publication that appeared prior to the filing of this application, but after the invention herein, discloses the cytoprotective actions of prostacyclin during hypoxia in the isolated perfused cat liver. The article reports that $PGI_2$ has a significant protective effect in hypoxic hepatocytes that may not be related to its vasodilation in inhibition of platelet aggregation. T. Mach, et al., J. for Clin. Res. and Practices Abst. of Xi Int. Cong. of Gastroenterol. June 8–13, 1980 (Hamburg) F 5.14, also appearing prior to the filing of this application but subsequent to the invention herein, reports a cytoprotective effect of 16,16-dimethyl Prostaglandin $E_2$ on acute galactosamine induced liver damage in the rat.

SUMMARY OF THE INVENTION

The present invention provides a method for the treatment or prevention of a hepatic disease in a mammal suffering from or particularly susceptible to the development of said disease which comprises:

systemically or orally administering to said mammal an amount of a hepatocytoprotective prostaglandin effective to treat or prevent said disease.

In accomplishing the purposes of this invention those compounds which are useful as hepatocytoprotective prostaglandins are those prostaglandins or prostaglandin analogs which are at least one tenth (0.1) as potent as $PGE_2$ in effecting a 50% reduction in liver necrosis in rats after carbon tetrachloride challenge as measured by a decrease in fat accumulation and glutamic pyruvic transaminase (SGPT) activity. This procedure is described in Example 1 below.

Thus prostaglandins of the E series, and analogs thereof, are useful as hepatocytoprotective agents. Examples of hepatocytoprotective prostaglandins are:

$PGE_2$;
(15R)-15-methyl-$PGE_2$;
16,16-dimethyl-$PGE_2$;
11-deoxy-11R-16,16-trimethyl-$PGE_2$;
11-deoxy-11R-16,16-trimethyl-$PGE_1$;
15-deoxy-16-hydroxy-16-methyl-$PGE_1$;
15-deoxy-16-hydroxy-16-methyl-$PGE_1$, methyl ester;
15-deoxy-16-hydroxy-16-methyl-$PGE_2$;
15-deoxy-16-hydroxy-16-methyl-$PGE_2$, methyl ester;
15-methyl-cis4,5-didehydro-$PGE_1$, methyl ester;
16,16-dimethyl-cis-4,5-didehydro-$PGE_1$, methyl ester;
17-phenyl-18,19,20-trinor-cis-4,5-didehydro-$PGE_1$, methyl ester;
5-oxa-16-(p-fluorophenoxy)-17,18,19,20-tetranor-$PGE_1$, methyl ester;
15-methyl-$PGE_1$;
16-phenoxy-17,18,19,20-tetranor-$PGE_1$;
cis-4,5-didehydro-16,16-dimethyl-$PGE_1$;
2,2-Difluoro-15methyl-$PGE_1$, methyl ester;
16,16-difluoro-5-oxa-$PGE_1$, methyl ester;
16,16-difluoro-13,14-dihydro-$PGE_1$, methyl ester;
15-methyl-$PGE_2$;
16-methyl-$PGE_2$;
15-methyl-$PGE_2$, methyl ester;
16,16-dimethyl-$PGE_2$;
17-phenyl-18,19,20-trinor-$PGE_2$;
17-cyclohexyl-18,19,20-trinor-$PGE_2$;
15-methyl-$PGE_2$, isopropyl ester;

15-methyl-PGE$_2$, p-acetamidophenyl ester;
11-deoxy-16,16-dimethyl-PGE$_2$;
16,16-difluoro-PGE$_2$, methyl ester;
16-phenoxy-17,18,19,20-tetranor-PGE$_2$;
13,14-didehydro-PGE$_2$, methyl ester;
17-phenyl-18,19,20-trinor-PGE$_2$, p-acetylphenyl ester;
15-methyl-17-phenyl-18,19,20-trinor-PGE$_2$, methyl ester;
17,18,19,20tetranor-16-phenoxy-PGE$_2$, p-acetylphenyl ester;
11-deoxy-16-phenoxy-17,18,19,20-tetranor-PGE$_2$;
15-methyl-16-phenoxy-17,18,19,20-tetranor-PGE$_2$, methyl ester;
15-epi-15-methyl-16-phenoxy-17,18,19,20-tetranor-PGE$_2$, methyl ester;
2a,2b-dihomo-17,18,19,20-tetranor-16-phenoxy-PGE$_2$;
11-deoxy-16,16-difluoro-PGE$_2$, methyl ester;
2a,2b-dihomo-15-methyl-17-phenyl-18,19,20-trinor-PGE$_2$, methyl ester;
13,14-didehydro-PGE$_2$;
2,2-difluoro-16-(m-trifluoromethyl phenoxy)-17,18,19,20-tetranor-PGE$_2$, 15-methyl ether, methyl ester;
2,2,16,16-tetrafluoro-PGE$_2$, methyl ester;
16,16-difluoro-13,14-dihydro-PGE$_2$, methyl ester.

The measurement of SGPT activity is a well-known useful and sensitive test to detect the presence of hepatic disease. Thus, moderate elevations (above 50 international units) are found in almost all forms of obstructive liver diseases. The highest levels (greater than 400 units) are seen in parenchymal (functional) liver disease, infectious hepititis (e.g., Type A, B, non-A, and non-B), infectious mononucleosis, toxic hepititis, and shock. In general, any elevation of SGPT to 50 international units or more indicates liver disease.

A "hepatic disease" is any disease of the liver which is characterized by an elevation of SGPT levels (excluding neoplastic diseases) and is readily diagnosed by an attending physician or veterinarian.

As noted above, the method of the present invention is effective in alleviating necrotic changes and/or fatty deposits in rats induced by carbon tetrachloride challenge. The method of the present invention is also useful in the alleviation of necrotic changes due to other liver diseases. The present invention is particularly useful in the treatment of liver damage induced by e.g., drug (including chemotherapy), infectious agents, and from diseases of unknown origin.

The present invention includes the treatment of each of various mammalian species, including humans. With respect to non-humans, the present invention is particularly and especially concerned with treating domesticated animals, for example, cattle, dogs, cats, and swine. By treatment is meant any alleviation of liver damage caused by a hepatic disease. By prevention is meant partial to total avoidance of liver damage from a hepatic disease, depending on the severity of the disease.

Any convenient route of administration is employed. Thus, oral formulation and oral administration is, for example, the preferred route for use in humans although parenteral (e.g., intravenous, intraperitoneal, and intramuscular) administration is also employed. See, e.g., U.S. Pat. No. 3,903,297 (Robert, "Method of Treatment in Prophylaxis of Gastric Hypersecretion in Gastric Acid and Duodenum Ulcers Using Prostaglandin Analogs"), issued September 2, 1975, columns 6-16 for some appropriate and well known means of administering the prostaglandins discussed herein.

The dosage regimen for the hepatocytoprotective prostaglandin in accord with this invention will depend on a variety of factors, including the type, age, weight, sex, and medical condition of the mammal, nature and severity of the hepatic disease and the particular hepatocytoprotective prostaglandin to be administered. It is within the skill of the attending physician or veterinarian to determine the presence of the hepatic disease, and to prescribe an effective amount of the hepatocytoprotective prostaglandin to reduce and then substantially to eliminate the necrotic changes of the liver. In doing that, the physician or veterinarian would by one method start at a relatively low dose of the hepatocytoprotective prostaglandin, for example, about 0.25 mg/kg/day to about 0.1 µg/kg, day, and observe the response of the human or animal patient for a few days. The dose of the hepatocytoprotective prostaglandin is then adjusted downward or upward until the maximum effective dose is found. For example, the maximum needed dose is usually between about 25 mg/kg/day and about 15 µg/kg/day although it may be necessary to occasionally exceed these doses when the hepatic disease is especially severe. Once the minimum effective dose of the particular hepatocytoprotective prostaglandin is determined for a particular subject, it is advantageous to provide the subject with the dosage schedule which will provide a substantially uniform level of hepatocytoprotective prostaglandin to the liver.

The employment of sound medical therapy requires that the hepatocytoprotective prostaglandin be employed prophylactically only in cases where the animal or patient is particularly susceptible to the development of an hepatic disease. The conditions and circumstances which increase the susceptibility are readily ascertainable to the ordinary skilled physician or veterinarian and include alcoholism, exposure to environmental (including infectious agents) and occupational toxins (e.g., carbon tetrachloride), exposure to hepatotoxic drugs (e.g., anesthetics), and gross obesity.

In the prophylactic use of these hepatocytoprotective prostaglandins, the dose effective for the prevention of an hepatic disease is readily determined by patient or animal response, as discussed above for therapeutic uses, and is, in general, somewhat less than the dose required to cure or treat the disease.

DESCRIPTION OF THE PREFERRED EMBODIMENTS

The operation of the present invention is seen more fully by the examples given below.

EXAMPLE 1

Groups of 4 female rats weighing between 200-216 g were given 1 ml oral doses of a vehicle, containing ethanol and a lipid solubilizing agent; (15R)-15-methyl-prostaglandin E$_2$ (100 µg/kg) or PGE$_2$ (0.3 mg/kg). Twenty-three and ½ hr later this treatment was repeated to be followed 30 min later by 1 ml of oral carbon tetrachloride. Six hrs later the vehicle and prostaglandin compounds were administered to the three groups of four rats. Twenty-four hrs after carbon tetrachloride treatment the rats were sacrificed by cardiac puncture.

The livers were scored from 0 to 4 for fat content based on liver color as follows:
0 = maroon
1 = uniform red 2=half white-half red
3=all white
4=all white with hemorrhagic patches.

This scale was applied in gradations of 0.5. SGPT levels were measured in the collected serum.

Liver damage was 2.38 for vehicle treated animals. Those receiving (15R)-15-methyl prostaglandin $E_2$ had a score of 0.5 and those receiving $PGE_2$ had a score of 0.25.

Animals receiving prostaglandin treatment had a statistically significant decrease in SGPT values.

SGPT in vehicle treated animals was 291.8 international units, a value significantly greater than that seen in rats treated (15R)-15-methyl prostaglandin $E_2$ (43.3 international units) or prostaglandin $E_2$ (13.75 international units).

The values in the prostaglandin treated animals compared favorably with those of normal animals receiving without carbon tetrachloride challenge. The liver score for these animals was 0.33 and the SGPT values were 17.75. In all cases the rats were allowed access to food and water throughout the experiment.

EXAMPLE 2

The conditions described above were repeated except that female rats weighing between 200–220 g were used. 16,16-dimethyl-$PGE_2$ was administered subcutaneously in quantities of 5, 25, and 75 per kg. Liver scores for animals receiving vehicle alone were 2.2; those receiving 5 μg per kg of the prostaglandin had a liver score of 1.75; those receiving the 25 μg per kg had a liver score of 1.00, and those receiving 75 μg per kg had a liver score of 0.92. SGPT scores were 401.2; 248; 177.5; and 84.3 for vehicle, 5, 25, and 75 μg per kg doses respectively.

I claim:

1. A method for the treatment or prevention of a hepatic disease characterized by glutamic pyruvic transaminase (SGPT) activity of greater than 50 international units in a mammal suffering from or particularly susceptible to the development of said disease which comprises:

systemically or orally administering to said mammal an amount of a hepatocytoprotective PGE-type prostaglandin effective to treat or prevent said disease.

2. A method according to claim 1 wherein said mammal is a human.

3. A method according to claim 2 wherein said hepatocytoprotective prostaglandin is administered prophylactically.

4. A method according to claim 2 wherein said hepatocytoprotective prostaglandin is administered therapeutically.

5. A method according to claim 4, wherein said prostaglandin is $PGE_2$.

6. A method according to claim 4, wherein said prostaglandin is 16,16-dimethyl-$PGE_2$.

7. A method according to claim 4, wherein said prostaglandin is (15R)-15-methyl-$PGE_2$.

* * * * *

UNITED STATES PATENT OFFICE
CERTIFICATE OF CORRECTION

Patent No. 4,374,856                Dated 22 February 1983

Inventor(s) M.J. Ruwart

It is certified that error appears in the above-identified patent and that said Letters Patent are hereby corrected as shown below:

Column 1, line 29, "modules" should read -- nodules --.
Column 2, line 59, "-15methyl-" should read -- -15-methyl- --.
Column 3, line 10, ",19,20tetranor-" should read -- ,19,20-tetranor- --.

Signed and Sealed this

*Twenty-fourth* Day of *May 1983*

[SEAL]

*Attest:*

DONALD J. QUIGG

*Attesting Officer*     *Acting Commissioner of Patents and Trademarks*